(12) United States Patent
Wang

(10) Patent No.: US 12,582,269 B2
(45) Date of Patent: Mar. 24, 2026

(54) INTELLIGENT TOOTHPASTE DISPENSING SYSTEM

(71) Applicant: SHENZHEN BESMAN ELECTRONIC TECHNOLOGY CO., LTD, Shenzhen (CN)

(72) Inventor: Xuewu Wang, Shenzhen (CN)

(73) Assignee: SHENZHEN BESMAN ELECTRONIC TECHNOLOGY CO., LTD, Shenzhen (CN)

( * ) Notice: Subject to any disclaimer, the term of this patent is extended or adjusted under 35 U.S.C. 154(b) by 378 days.

(21) Appl. No.: 18/302,169

(22) Filed: Apr. 18, 2023

(65) Prior Publication Data

US 2024/0032738 A1 Feb. 1, 2024

(30) Foreign Application Priority Data

Aug. 1, 2022 (CN) .......................... 202210915516.3

(51) Int. Cl.
A47K 5/18 (2006.01)
A47K 5/12 (2006.01)
G16H 20/00 (2018.01)

(52) U.S. Cl.
CPC .............. A47K 5/18 (2013.01); A47K 5/1217 (2013.01); G16H 20/00 (2018.01)

(58) Field of Classification Search
CPC .... A61B 5/4547; G16H 50/30; A47K 5/1217; A47K 5/18

USPC ........................................................ 700/233
See application file for complete search history.

(56) References Cited

U.S. PATENT DOCUMENTS 11,127,312 B2 * 9/2021 Felder .................. A61C 15/043
11,884,440 B2 * 1/2024 Xing ...................... G05B 15/02
2009/0293211 A1 * 12/2009 Spungin ............. A46B 15/0055
                                                              15/105
2018/0184857 A1 * 7/2018 Pai .......................... A46B 3/005

* cited by examiner

*Primary Examiner* — Timothy R Waggoner
(74) *Attorney, Agent, or Firm* — HOWARD M COLIN and Associates, LLC

(57) ABSTRACT

An intelligent toothpaste dispensing system includes an intelligent toothbrush, a sampling sensor, and an intelligent toothpaste mixing dispenser. The intelligent toothbrush and the sampling sensor realize data interaction transmission with the intelligent toothpaste mixing dispenser through a wireless communication module. A dispenser circuit board component is arranged on the intelligent toothpaste mixing dispenser. The dispenser circuit board component includes a formula database and a data comparison module. After the data comparison module receives sampling data from the sampling sensor, the data comparison module compares the sampling data with the formula database and extracts a mixing formula. According to a mixing formula instruction, the data comparison module drives the intelligent toothpaste mixing dispenser to mix and dispense toothpaste ingredients and extrude toothpaste consistent with the mixing formula.

10 Claims, 3 Drawing Sheets

INTELLIGENT TOOTHPASTE DISPENSING SYSTEM

TECHNICAL FIELD

The present disclosure relates to a technical field of intelligent control devices, and in particular to an intelligent toothpaste dispensing system.

BACKGROUND

Toothpastes, which have a long history, are a common cleaning product in daily life. With continuous development of science and technology, and with continuous improvement and perfection of technology and equipment, various types of toothpastes are created. Quality and grade of the toothpastes are continuously improved. Nowadays, the toothpastes have developed from a single type of cleaning toothpastes to multi-functional toothpastes having a full range of varieties, diverse functions, and hundreds of brands, which meet needs of different levels of consumption.

However, toothpastes sold in the market are all finished toothpastes filled by manufacturers after pre-blending ingredients. Although it is undeniable that most of the toothpastes maintain certain medicinal functions by prefabrication in advance, it is clear that medicinal properties of the toothpastes are significantly reduced after a long time of immersion reaction according to chemical principles, which not only results in a large waste of resources, but also such toothpastes cannot meet the use criteria in terms of the demand for a strong chemical activity of the toothpastes. Moreover, in daily oral care and treatment process, it is necessary to mix quantitative formula of the toothpaste to achieve intended using effect sometimes, and the conventional pre-made toothpastes made by filling are unable to meet such demands.

As the old saying goes, "disease enters from the mouth", the mouth is an entrance to respiratory and digestive tract, and has important physiological functions such as chewing, swallowing, and speech expression. It is one of the important ways for pathogenic microorganisms to invade our bodies, and also a direct port for people to understand their own health status. For example, through breath or oral secretions, many health indexes may be detected. Therefore, daily routine sampling of oral environment and scientific and effective health management are conducive to improving protection of human health. However, due to the fast pace of modern people's hives, most of time in a day people are busy in work and trifles. It is difficult to spare time, or simply unable to conduct regular health testing, which has laid an unpredictable hidden danger to people's health. Therefore, if people are able to utilize daily tooth brushing to carry out routine testing of human health, through scientific long-term monitoring and management of human body state, undoubtedly it achieves good health management without time loss.

SUMMARY

A purpose of the present disclosure is to provide an intelligent toothpaste dispensing system, which automatically identifies user IP information by means of intelligent system control, directly analyzes and obtains a real-time health index of a user through a sampling sensor and a data comparison module, and extracts a suitable toothpaste formula from a formula database after analyzing the real-time health index combined with the user's historical health file data. Toothpaste ingredients are automatically dispensed and mixed by an intelligent toothpaste mixing dispenser according to the toothpaste formula, and then mixed toothpaste is extruded for the user to use, thus playing the effect of oral care and health monitoring. A use process is intelligently analyzed and controlled by the intelligent toothpaste dispensing system, which is convenient to use and achieves effective oral and physical health management without taking up the user's extra time, thus solving problems mentioned in the prior art.

To achieve the above purpose, the present disclosure provides the intelligent toothpaste dispensing system. The intelligent toothpaste dispensing system comprises an intelligent toothbrush, a sampling sensor, and an intelligent toothpaste mixing dispenser. The intelligent toothbrush and the sampling sensor realize data interaction transmission with the intelligent toothpaste mixing dispenser through a wireless communication module. A dispenser circuit board component is arranged on the intelligent toothpaste mixing dispenser. The dispenser circuit board component comprises a formula database and a data comparison module. After the data comparison module receives sampling data from the sampling sensor, the data comparison module compares the sampling data with the formula database and extracts a mixing formula. According to a mixing formula instruction, the data comparison module drives the intelligent toothpaste mixing dispenser to mix and dispense toothpaste ingredients and extrude toothpaste consistent with the mixing formula.

Optionally, a signal triggering device is arranged on the intelligent toothbrush. The signal triggering device switches the intelligent toothpaste mixing dispenser from a static state to a standby state.

Optionally, the signal triggering device is a gyroscope.

Optionally, user IP information is stored in the intelligent toothbrush. The dispenser circuit board component is packaged with an information reading module. The dispenser circuit board component is connected to a file database. The information reading module precisely reads the user IP information and retrieves a corresponding user file from the file database. The corresponding user file is compared and updated by the data comparison module.

Optionally, the sampling sensor is installed inside a shell of the intelligent toothbrush. An air blowing window is defined on a position, corresponding to the sampling sensor, of the intelligent toothbrush. The air blowing window runs through the shell.

Optionally, the intelligent toothpaste mixing dispenser comprises a housing. A first support and a second support are arranged inside the housing. A first storage bin is detachably arranged on the first support. A second storage bin is detachably arranged on the second support. The toothpaste ingredients are respectively stored in the first storage bin and the second storage bin. An extraction device is arranged in the housing. The extraction device defines an input end and an output end. The input end of the extraction device is communicated with the first storage bin and the second storage bin through pipes. The output end of the extraction device is communicated with an extruding bin. Flow control devices are respectively arranged between the extraction device and the first storage bin, between the extraction device and the second storage bin, and between the extraction device and the extruding bin. The flow control devices precisely control output quantity of the toothpaste ingredients according to flow values determined by the mixing formula. The extraction device and the flow control devices are electrically connected to the dispenser circuit board component.

Optionally, the extraction device is an air pump and the flow control devices are solenoid valves.

Optionally, a battery is arranged in the housing. The housing defines a display through hole. A touch screen is embedded in the display through hole. The battery and the touch screen are electrically connected to the dispenser circuit board component. The dispenser circuit board component is electrically connected to a USB interface and a switch button. The USB interface and the switch button are arranged in through holes defined on the housing. The USB interface and the switch button extend outwards from the through holes.

Optionally, the extruding bin comprises an opening cover embedded in the housing and an extruding nozzle. A first end of the extruding nozzle passes through the opening cover. A main body of the extruding nozzle is arranged in an inner side of the opening cover. A second end of the extruding nozzle is communicated with an output end of the extraction device. A position sensor is arranged inside the extruding bin.

Optionally, the dispenser circuit board component is electrically connected to a timer arranged on the dispenser circuit board component. The timer controls an output duration of the output end of the extraction device.

Compared with the prior art, in the present disclosure, the intelligent toothpaste dispensing system automatically identifies user IP information by means of intelligent system control, directly analyzes and obtains the real-time health index of the user through the sampling sensor and the data comparison module, and extracts the suitable toothpaste formula from the formula database after analyzing the real-time health index combined with the user's historical health file data. The toothpaste ingredients are automatically dispensed and mixed by the intelligent toothpaste mixing dispenser according to the toothpaste formula, and then the mixed toothpaste is extruded for the user to use, thus playing the effect of oral care and health monitoring. The use process is intelligently analyzed and controlled by the intelligent toothpaste dispensing system, which is convenient to use and achieves effective oral and physical health management without taking up user's extra time.

Figure 1:
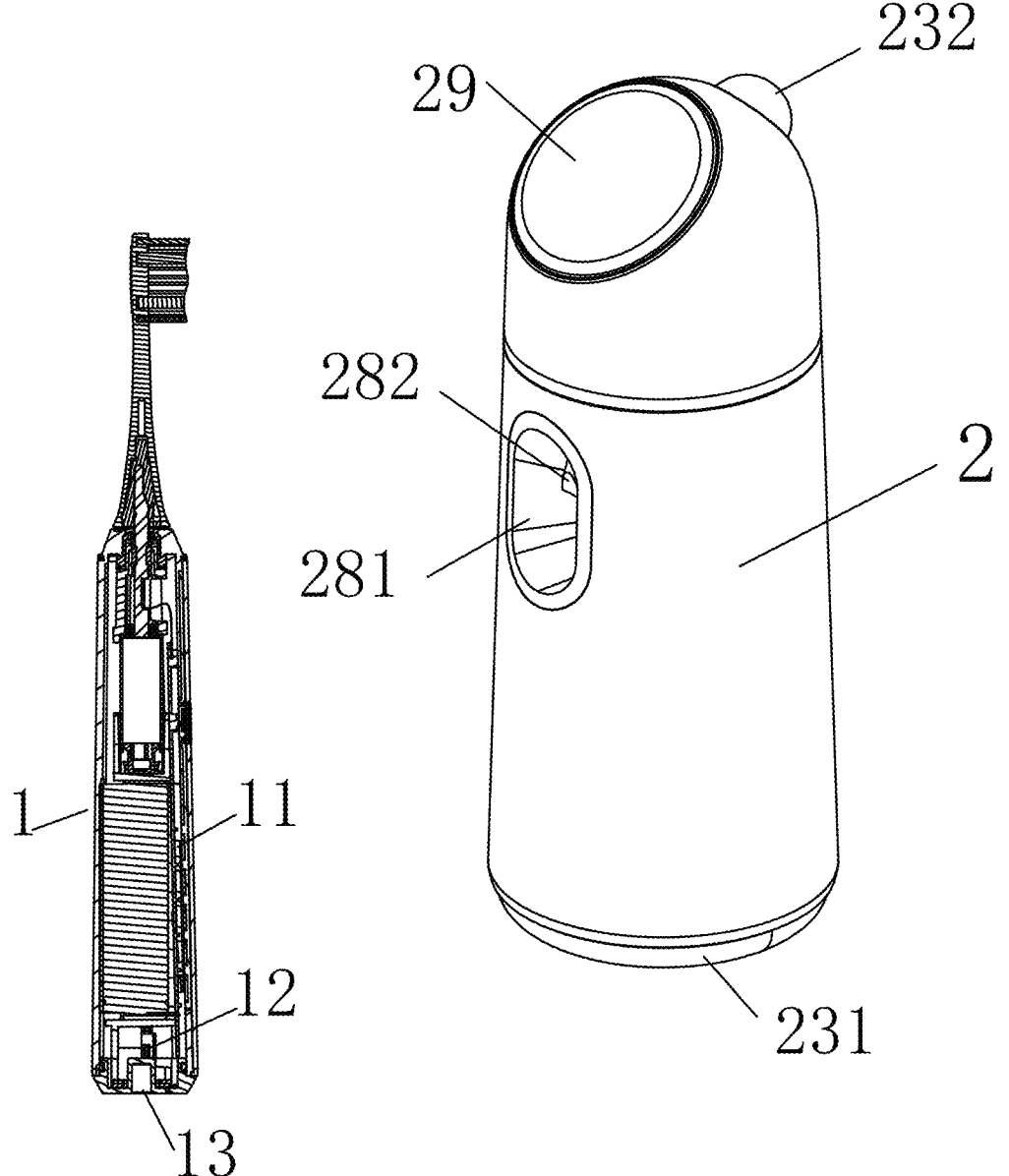
FIG. 1 is a structural schematic diagram of an intelligent toothbrush and an intelligent toothpaste mixing dispenser of the present disclosure.

In the drawings: 1—intelligent toothbrush; 11—gyroscope; 12—sampling sensor; 13—air blowing window; 2—intelligent toothpaste mixing dispenser; 21—housing; 211—display through hole; 221—first support; 222—second support; 231—first storage bin; 232—second storage bin; 24—solenoid valve; 25—dispenser circuit board component; 251—USB interface; 252—switch button; 26—air pump; 27—battery; 28—extruding bin; 281—opening cover; 282—extruding nozzle; 283—position sensor; 29—touch screen.

DETAILED DESCRIPTION

The technical solutions of embodiments of the present disclosure will be clearly and completely described below in conjunction with the attached drawings of the embodiments of the present disclosure. Obviously, the described embodiments are only a part of the embodiments of the present disclosure, not all of the embodiments. Based on the embodiments in the present disclosure, all other embodiments obtained by those skilled in the art without making creative labor should fall within the protection scope of the present disclosure.

Figure 2:
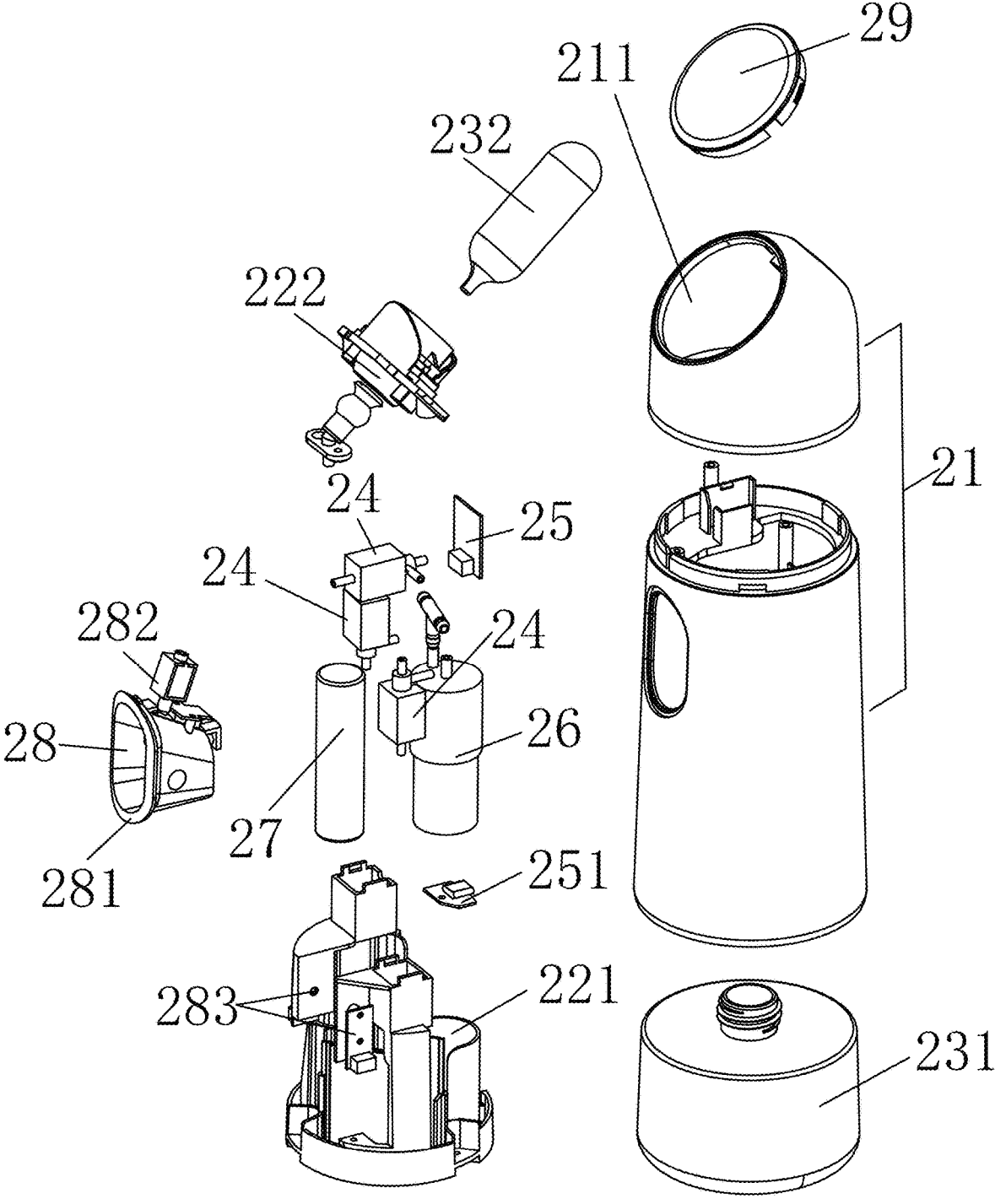
FIG. 2 is an exploded schematic diagram of the intelligent toothpaste mixing dispenser of the present disclosure.
Figure 3:
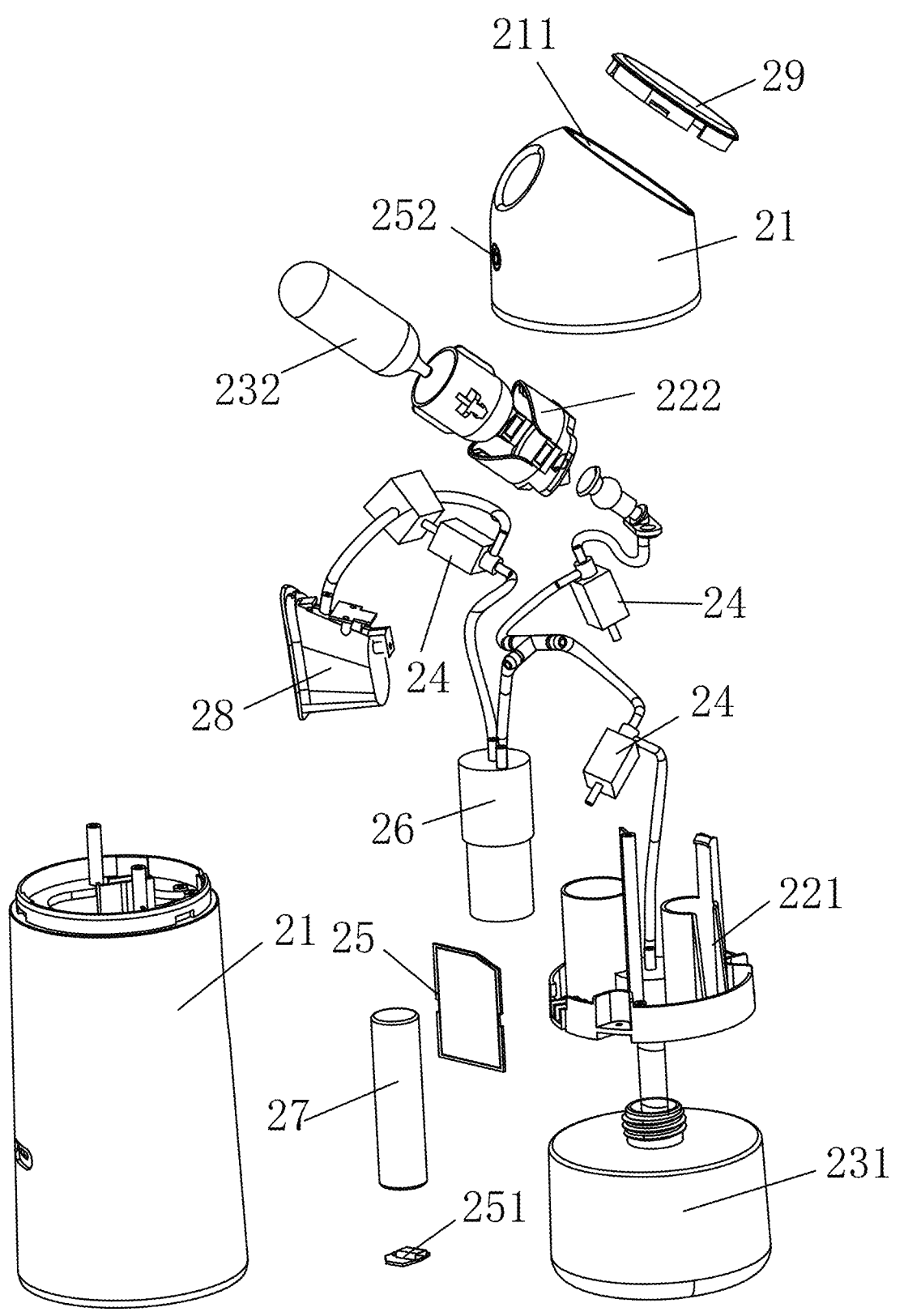
FIG. 3 is a schematic diagram of pipes of the intelligent toothpaste mixing dispenser of the present disclosure.

As shown in FIGS. 1-3, the present disclosure provides an intelligent toothpaste dispensing system. The intelligent toothpaste dispensing system comprises an intelligent toothbrush 1, a sampling sensor 12, and an intelligent toothpaste mixing dispenser 2. A signal triggering device is arranged in the intelligent toothbrush 1. The signal triggering device switches the intelligent toothpaste mixing dispenser 2 from a static state to a standby state. The signal triggering device is a gyroscope 11. The intelligent toothbrush 1 and the sampling sensor 12 realize data interaction transmission with the intelligent toothpaste mixing dispenser 2 through a wireless communication module. When the intelligent toothbrush 1 in the static state and is picked up to generate displacement or to change in position, the gyroscope 11 is triggered and sends a wake-up instruction through the wireless communication module to the intelligent toothpaste mixing dispenser 2. After the intelligent toothpaste mixing dispenser 2 is woken up for 30 seconds without any operation, the intelligent toothbrush 1 enters the standby state again, and a touch screen is off. The wireless communication module is a BLUETOOTH module. User IP information is stored in the intelligent toothbrush 1. An information reading module is packaged on the dispenser circuit board component 25. The dispenser circuit board component 25 is connected to a file database. When the gyroscope 11 is triggered and turns on the intelligent toothpaste mixing dispenser 2, the information reading module precisely reads the user IP information and retrieves a corresponding user file information from the file database. The corresponding user file information is loaded in the intelligent toothpaste mixing dispenser 2. The dispenser circuit board component 25 is arranged on the intelligent toothpaste mixing dispenser 2. The dispenser circuit board component 25 comprises a formula database and a data comparison module. The sampling sensor 12 is installed in a shell of the intelligent toothbrush 1. The shell of the intelligent toothbrush 1 defines an air blowing window 13 corresponding to a position of the sampling sensor 12. The air blowing window 13 runs through the shell. Before using the intelligent toothbrush 1, a user can blow into the air blowing window 13. At this time, the sampling sensor 12 sends sampling data of blowing to the data comparison module after collecting the sampling data of blowing. The data comparison module receives the sampling data, compares and analyzes the sampling data with user's historical health file data, and finally extracts a mixing formula by comparing a comprehensive analysis comparing result with the formula database. Then, according to a mixing formula instruction, the intelligent toothpaste mixing dispenser 2 is driven to dispense and mix toothpaste ingredients and extrude the toothpaste consistent with the mixing formula. After brushing, the user blows into air window 13 again, and the sampling sensor 12 takes a sample and analyzes again. Then sampling sensor 12 outputs brushing effect information through the touch screen 29, updates and saves user's historical health file data.

For hardware part, the intelligent toothpaste mixing dispenser 2 comprises a housing 21 and storage bins. A first support 221 and a second support 222 are arranged inside the housing 21. The storage bins comprise a first storage bin 231 and a second storage bin 232. The first support 221 is detachably connected with the first storage bin 231, and the second support is detachably connected with the second storage bin 232. The toothpaste ingredients are respectively stored in the first storage bin 231 and the second storage bins. The housing 21 is equipped with an extraction device. The extraction device is air pump 26. The extraction device defines an input end and an output end. The input end of the extraction device is communicated with the first storage bin 231 and the second storage bin 232 through pipes; The output end of the extraction device is communicated with an extruding bin 28. Flow control devices are respectively arranged between the extraction device and each of the storage bins and between the extraction device and the extruding bin 28. The flow control device is solenoid valve 24. The flow control devices precisely control output quantity of the toothpaste ingredients according to flow values determined by the mixing formula. The extraction device and the flow control devices are electrically connected to the dispenser circuit board component 25. The extruding bin 28 comprises an opening cover 281 embedded in the housing 21 and an extruding nozzle 282. A first end of the extruding nozzle 282 passes through the opening cover 281. A main body of the extruding nozzle 282 is arranged in an inner side of the opening cover 281. A second end of the extruding nozzle 282 is communicated with an output end of the extraction device. A position sensor 283 is arranged inside the extruding bin 28.

When a toothbrush head of the intelligent toothbrush 1 sticks into the extruding bin 28, the position sensor 283 identifies insertion state of the toothbrush head. When the toothbrush head reaches a designated position, extraction device is activated to extrude toothpaste onto bristles of the toothbrush head through the extruding nozzle 282. The dispenser circuit board component 25 is electrically connected to a timer, through which the volume of toothpaste extruded is controlled.

A battery 27 is arranged in the housing 21. The housing 21 defines a display through hole 211; a touch screen 29 is embedded in the display through hole 211. The battery 27 and the touch screen 29 are electrically connected to the dispenser circuit board component 25. A circuit control function of the intelligent toothpaste mixing dispenser 2 is set by controlling the touch screen 29.

The dispenser circuit board component 25 is electrically connected to a USB interface 251 and a switch button 252. The USB interface 251 and the switch button 252 are arranged in through holes defined on the housing 21. The USB interface 251 and the switch button 252 extend outwards from the through holes.

The USB interface 251 is connected to an external power supply via a USB cable. The external power supply charges the battery 27 or provides electricity for the intelligent toothpaste mixing dispenser 2. The switch button 252 is configured to control opening and closing states of a main circuit of the intelligent toothpaste mixing dispenser 2.

In conclusion, in the present disclosure, the intelligent toothpaste dispensing system automatically identifies the user IP information by means of intelligent system control, directly analyzes and obtains a real-time health index of the user through the sampling sensor 12 and the data comparison module, and extracts the suitable toothpaste formula from the formula database after analyzing the real-time health index combined with the user's historical health file data. The toothpaste ingredients are automatically dispensed and mixed by the intelligent toothpaste mixing dispenser 2 according to the toothpaste formula, and then the mixed toothpaste is output for the user to use, thus playing effect of oral care and health monitoring. The use process is intelligently analyzed and controlled by the intelligent toothpaste dispensing system, which is convenient to use and achieves effective oral and physical health management without taking up user's extra time.

It should be noted that, in the present disclosure, relational terms, such as "first" and "second", are only used to distinguish one feature or operation from another feature or operation, and do not necessarily require or imply any actual relationship or sequence exists between these features or operations. Moreover, terms "comprise", "include" or any other variation thereof are intended to encompass non-exclusive inclusion, such that a process, method, article or device not only comprises elements explicitly listed, but also comprises elements not explicitly listed or other elements inherent to such a process, method, article or device.

Although embodiments of the present disclosure have been shown and described, for those general technical staff in the field, it is understandable that a variety of variations, modifications, replacements and variants of these embodiments can be made without departing from principles and spirit of the present disclosure, the scope of which is limited by appended claims and their equivalents.

Although the embodiments of the present disclosure have been shown and described, those of ordinary skill in the art can understand that various changes, modifications, substitutions, and variations can be made to these embodiments without departing from the principle and spirit of the present disclosure. The scope of the present disclosure is defined by the appended claims and their equivalents.

What is claimed is:

1. An intelligent toothpaste dispensing system, comprising:

an intelligent toothbrush, a sampling sensor, and an intelligent toothpaste mixing dispenser;

wherein the intelligent toothbrush and the sampling sensor realize data interaction transmission with the intelligent toothpaste mixing dispenser through a wireless communication module; a dispenser circuit board component is arranged on the intelligent toothpaste mixing dispenser; the dispenser circuit board component comprises a formula database and a data comparison module; after the data comparison module receives sampling data from the sampling sensor, the data comparison module compares the sampling data with the formula database and extracts a mixing formula; according to a mixing formula instruction, the data comparison module drives the intelligent toothpaste mixing dispenser to mix and dispense toothpaste ingredients and extrude toothpaste consistent with the mixing formula.

2. The intelligent toothpaste dispensing system according to claim 1, wherein a signal triggering device is arranged on the intelligent toothbrush; the signal triggering device switches the intelligent toothpaste mixing dispenser from a static state to a standby state.

3. The intelligent toothpaste dispensing system according to claim 2, wherein the signal triggering device is a gyroscope.

4. The intelligent toothpaste dispensing system according to claim 1, wherein user IP information is stored in the intelligent toothbrush; the dispenser circuit board component is packaged with an information reading module; the dispenser circuit board component is connected to a file database; the information reading module precisely reads the user IP information and retrieves a corresponding user file from the file database; the corresponding user file is compared and updated by the data comparison module.

5. The intelligent toothpaste dispensing system according to claim 1, wherein the sampling sensor is installed inside a shell of the intelligent toothbrush; an air blowing window is defined on a position, corresponding to the sampling sensor, of the intelligent toothbrush; the air blowing window runs through the shell.

6. The intelligent toothpaste dispensing system according to claim 1, wherein the intelligent toothpaste mixing dispenser comprises a housing; wherein a first support and a second support are arranged inside the housing; a first storage bin is detachably arranged on the first support; a second storage bin is detachably arranged on the second support; the toothpaste ingredients are respectively stored in the first storage bin and the second storage bin;

wherein an extraction device is arranged in the housing: the extraction device defines an input end and an output end; the input end of the extraction device is communicated with the first storage bin and the second storage bin through pipes; the output end of the extraction device is communicated with an extruding bin;

wherein flow control devices are respectively arranged between the extraction device and the first storage bin, between the extraction device and the second storage bin, and between the extraction device and the extruding bin the flow control devices precisely control output quantity of the toothpaste ingredients according to flow values determined by the mixing formula: the extraction device and the flow control devices are electrically connected to the dispenser circuit board component.

7. The intelligent toothpaste dispensing system according to claim 6, wherein the extraction device is an air pump and the flow control devices are solenoid valves.

8. The intelligent toothpaste dispensing system according to claim 6, wherein a battery is arranged in the housing; the housing defines a display through hole; a touch screen is embedded in the display through hole; the battery and the touch screen are electrically connected to the dispenser circuit board component; the dispenser circuit board component is electrically connected to a USB interface and a switch button; the USB interface and the switch button are arranged in through holes defined on the housing; the USB interface and the switch button extend outwards from the through holes.

9. The intelligent toothpaste dispensing system according to claim 6, wherein the extruding bin comprises an opening cover embedded in the housing and an extruding nozzle; a first end of the extruding nozzle passes through the opening cover; a main body of the extruding nozzle is arranged in an inner side of the opening cover; a second end of the extruding nozzle is communicated with an output end of the extraction device; a position sensor is arranged inside the extruding bin.

10. The intelligent toothpaste dispensing system according to claim 9, wherein the dispenser circuit board component is electrically connected to a timer arranged on the dispenser circuit board component; the timer controls an output duration of the output end of the extraction device.

\* \* \* \* \*